United States Patent
Lee

(10) Patent No.: US 10,986,996 B2
(45) Date of Patent: Apr. 27, 2021

(54) REMOVABLE OPTICAL COHERENCE TOMOGRAPHY (OCT) DEVICE

(71) Applicant: KOH YOUNG TECHNOLOGY INC., Seoul (KR)

(72) Inventor: Hyun Ki Lee, Daegu (KR)

(73) Assignee: KOH YOUNG TECHNOLOGY INC., Seoul (KR)

( * ) Notice: Subject to any disclaimer, the term of this patent is extended or adjusted under 35 U.S.C. 154(b) by 1137 days.

(21) Appl. No.: 15/313,701

(22) PCT Filed: May 27, 2015

(86) PCT No.: PCT/KR2015/005324
§ 371 (c)(1),
(2) Date: Nov. 23, 2016

(87) PCT Pub. No.: WO2015/182995
PCT Pub. Date: Dec. 3, 2015

(65) Prior Publication Data
US 2017/0188833 A1    Jul. 6, 2017

(30) Foreign Application Priority Data
May 27, 2014    (KR) ........................ 10-2014-0063402

(51) Int. Cl.
*A61B 5/00*    (2006.01)
*A61B 1/05*    (2006.01)
(Continued)

(52) U.S. Cl.
CPC ........ *A61B 5/0066* (2013.01); *A61B 1/00163* (2013.01); *A61B 1/05* (2013.01);
(Continued)

(58) Field of Classification Search
CPC ... A61B 5/0066; A61B 10/00; A61B 1/00163; A61B 1/05; A61B 2560/0443;
(Continued)

(56) References Cited

U.S. PATENT DOCUMENTS 5,795,295 A    8/1998    Hellmuth et al.
6,485,413 B1 *   11/2002    Boppart ............. A61B 1/00096
                                                    356/450
(Continued)

FOREIGN PATENT DOCUMENTS

CN         2303267      1/1999
CN         1703609      11/2005
(Continued)

OTHER PUBLICATIONS

Written Opinion with English Translation for International Application No. PCT/KR2015/005324, dated Jun. 30, 2015.
(Continued)

*Primary Examiner* — Mohamed K Amara
(74) *Attorney, Agent, or Firm* — Kile Park Reed & Houtteman PLLC

(57) ABSTRACT

The present disclosure relates to an OCT device, which can be simply mounted without changing the structure of a microscope or an endoscope, thereby realizing an OCT system and, more particularly, to a removable OCT device including: a tunable laser configured to emit light to the light output side of an optical device by tuning the wavelength of the light; a first beam splitter installed on a path of the light emitted from the tunable laser; and a reference mirror installed on a path of the light that has passed through the first beam splitter, wherein the removable OCT device is mounted at the light output side of the optical device.

15 Claims, 5 Drawing Sheets

(51) Int. Cl.
*G02B 21/00* (2006.01)
*G01B 9/02* (2006.01)
*A61B 10/00* (2006.01)
*A61B 1/00* (2006.01)
*G02B 21/36* (2006.01)

(52) U.S. Cl.
CPC ............... *A61B 10/00* (2013.01); *G01B 9/02* (2013.01); *G01B 9/02091* (2013.01); *G02B 21/00* (2013.01); *G02B 21/361* (2013.01); *G02B 21/362* (2013.01); *A61B 2560/0443* (2013.01)

(58) Field of Classification Search
CPC ...... A61B 1/128; G02B 21/00; G02B 21/361; G02B 21/362; G01B 9/02; G01B 9/02091; G01N 21/17
See application file for complete search history.

(56) References Cited

U.S. PATENT DOCUMENTS

| | | | |
|---|---|---|---|
| 7,315,380 | B2 | 1/2008 | Chapman et al. |
| 7,872,759 | B2* | 1/2011 | Tearney ................. G01N 21/25 356/479 |
| 9,949,635 | B2* | 4/2018 | Nakanishi ................ A61B 3/14 |
| 10,548,715 | B2* | 2/2020 | Culbertson ............... A61F 2/16 |
| 10,548,716 | B2* | 2/2020 | Culbertson ........... A61F 2/1613 |
| 2002/0089586 | A1 | 7/2002 | Suzuki et al. |
| 2005/0254062 | A1 | 11/2005 | Tan et al. |
| 2007/0070356 | A1 | 3/2007 | Tan et al. |
| 2007/0132852 | A1 | 6/2007 | Yu |
| 2007/0187632 | A1 | 8/2007 | Igarashi |
| 2007/0299309 | A1* | 12/2007 | Seibel .................. A61B 1/0638 600/117 |
| 2008/0144039 | A1 | 6/2008 | Tan et al. |
| 2008/0186505 | A1 | 8/2008 | Tan et al. |
| 2009/0115964 | A1* | 5/2009 | Ueno .................... A61B 3/102 351/206 |
| 2009/0122320 | A1 | 5/2009 | Petersen et al. |
| 2010/0033676 | A1 | 2/2010 | De Vries et al. |
| 2010/0097616 | A1 | 4/2010 | Nebosis et al. |
| 2010/0238453 | A1 | 9/2010 | Tan et al. |
| 2010/0321700 | A1 | 12/2010 | Hirose et al. |
| 2011/0149291 | A1 | 6/2011 | Yamakita |
| 2011/0202044 | A1* | 8/2011 | Goldshleger .......... A61B 3/102 606/4 |
| 2011/0273668 | A1 | 11/2011 | Hirose |
| 2012/0026312 | A1 | 2/2012 | Sander |
| 2012/0300217 | A1* | 11/2012 | Yuasa ................... G06T 7/0002 356/479 |
| 2013/0278935 | A1 | 10/2013 | Yamada |
| 2014/0098829 | A1 | 4/2014 | Lewandowski et al. |
| 2014/0309527 | A1* | 10/2014 | Namati ................. G06T 7/0012 600/427 |
| 2019/0254514 | A1* | 8/2019 | Westphal ............. A61B 3/0083 |

FOREIGN PATENT DOCUMENTS

| | | |
|---|---|---|
| CN | 1875243 | 12/2006 |
| CN | 101002670 | 7/2007 |
| CN | 101677767 | 3/2010 |
| CN | 102264281 | 11/2011 |
| EP | 1 962 079 | 8/2008 |
| EP | 2 124 718 | 10/2012 |
| JP | 60-140916 | 9/1985 |
| JP | 2-140714 | 5/1990 |
| JP | 9-292575 | 11/1997 |
| JP | 10-71158 | 3/1998 |
| JP | 10-165362 | 6/1998 |
| JP | 2004-73667 | 3/2004 |
| JP | 2007-166578 | 6/2007 |
| JP | 2008-170363 | 7/2008 |
| JP | 2011-128109 | 6/2011 |
| JP | 2012-010775 | 1/2012 |
| JP | 2012-32813 | 2/2012 |
| JP | 2012-100713 | 5/2012 |
| JP | 2013-178235 | 9/2013 |
| KR | 10-2010-0103188 | 9/2010 |
| KR | 10-1053222 | 8/2011 |
| KR | 10-1253949 | 4/2013 |
| WO | 2011/158849 | 12/2011 |
| WO | 2012/002302 | 1/2012 |

OTHER PUBLICATIONS

Japanese Office Action with English translation dated Oct. 30, 2018 by the JPO for Japanese counterpart Patent Application No. 2016-569852.

International Search Report for International Application No. PCT/KR2015/005324, dated Jun. 30, 2015.

Japanese Office Action with English translation dated May 29, 2018 by the JPO for Japanese counterpart Application No. 2016-569852.

* cited by examiner

REMOVABLE OPTICAL COHERENCE TOMOGRAPHY (OCT) DEVICE

TECHNICAL FIELD

The present invention relates to a removable OCT (Optical Coherence Tomography) device and, more particularly, to an OCT device which can be simply mounted without changing the structure of a microscope or an endoscope to implement an OCT system.

BACKGROUND ART

An OCT device is a device capable of taking tomography images of a human body using interference of light in the infrared band. At the initial stage of technology development, it was possible to obtain images of several frames per second by changing the optical path mechanically. Nowadays, tomography images of several hundred frames per second can be taken by employing a three-dimensional OCT technique that makes use of a wavelength tunable laser and a high-speed digitizer.

FIG. 1, shows a conventional OCT device and a microscope equipped with the OCT device. The conventional OCT device captures tomography images with an interference signal of the signal light and the reference light by bypassing the light of an object incident on the microscope.

However, since the OCT device of the type shown in FIG. 1 requires a portion (A) (a beam splitter or the like) of the OCT device to be interposed between the main body of the microscope or the like and the objective lens (B) in order to bypass the signal light. This raises a problem that installation of the OCT device is difficult and that the alignment of precision equipment such as a microscope or the like is disturbed.

FIG. 2, shows an endoscope in which an OCT device is integrally formed. The endoscope in which the OCT device is integrally formed therewith can simultaneously perform the functions of the endoscope and the OCT device because a transducer and a optical fiber for a light source are formed within the endoscope.

However, the OCT device of the type shown in FIG. 2 suffers from a problem that all existing conventional endoscopes should be discarded and replaced by new ones, which leads to excessive waste of resources.

SUMMARY

Embodiments of the present disclosure solve the problems mentioned above. In some embodiments, a removable OCT device is capable of being easily installed and removed and minimizing a change of an existing optical device such as a microscope.

A removable OCT device according to one embodiment includes: a tunable laser configured to emit light to a light output side of an optical device by tuning a wavelength of the light; a first beam splitter installed on a path of the light emitted from the tunable laser; and a reference mirror installed on a path of the light that has passed through the first beam splitter, wherein the removable OCT device is mounted at the light output side of the optical device.

The removable OCT device may be used in state in which the removable OCT device is mounted on the light output side of an existing optical device. It is therefore possible to remarkably reduce the risk of misalignment or damage of the existing optical device.

Furthermore, the removable OCT device may be mounted while maintaining the existing optical device. It is therefore possible to use the existing optical device without having to discard the same.

Moreover, the removable OCT device may be easily attached and detached. It is therefore possible to use the OCT device by installing the same in one or more optical devices.

DETAILED DESCRIPTION

A removable OCT device according to the present disclosure will now be described in detail with reference to the accompanying drawings.

Figure 1:
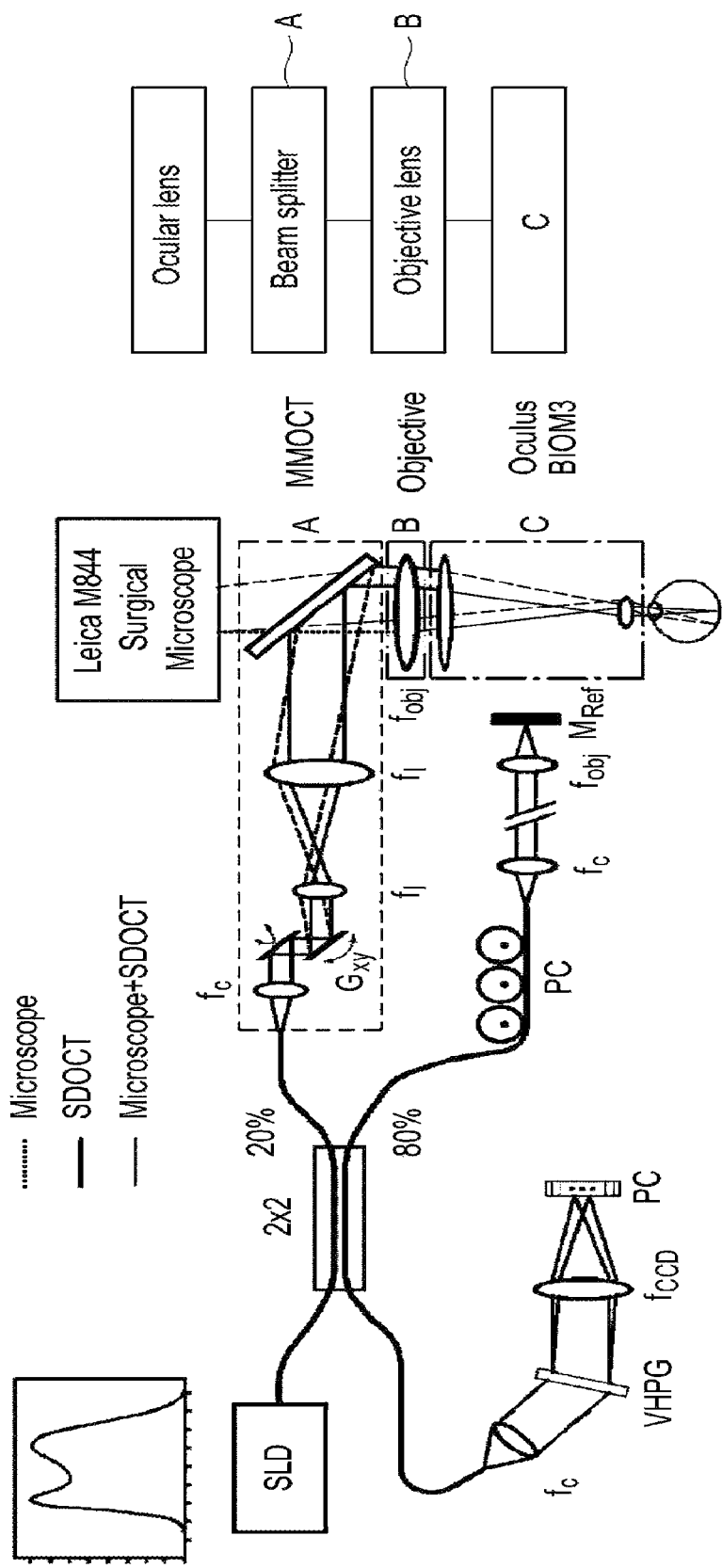
FIG. 1 shows a conventional OCT device and a microscope equipped with the OCT device.
Figure 2:
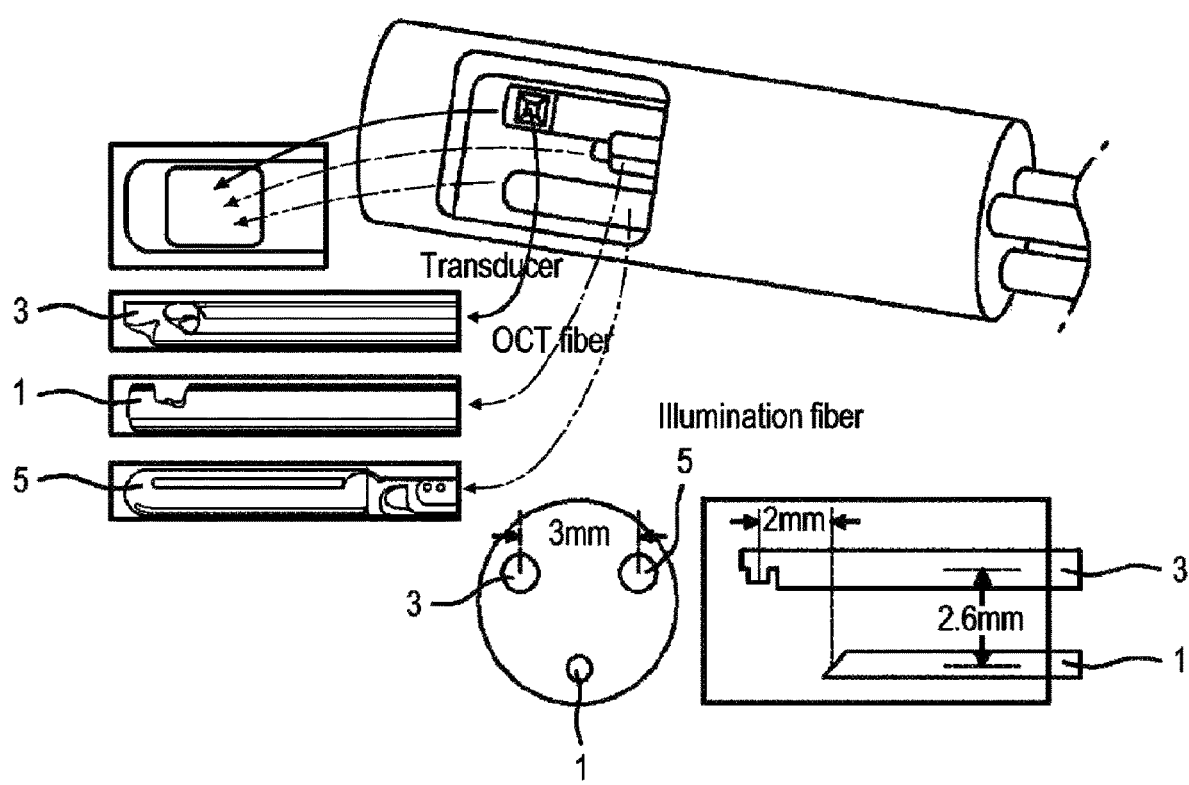
FIG. 2 shows an endoscope with which the OCT device is integrally formed.
Figure 3:
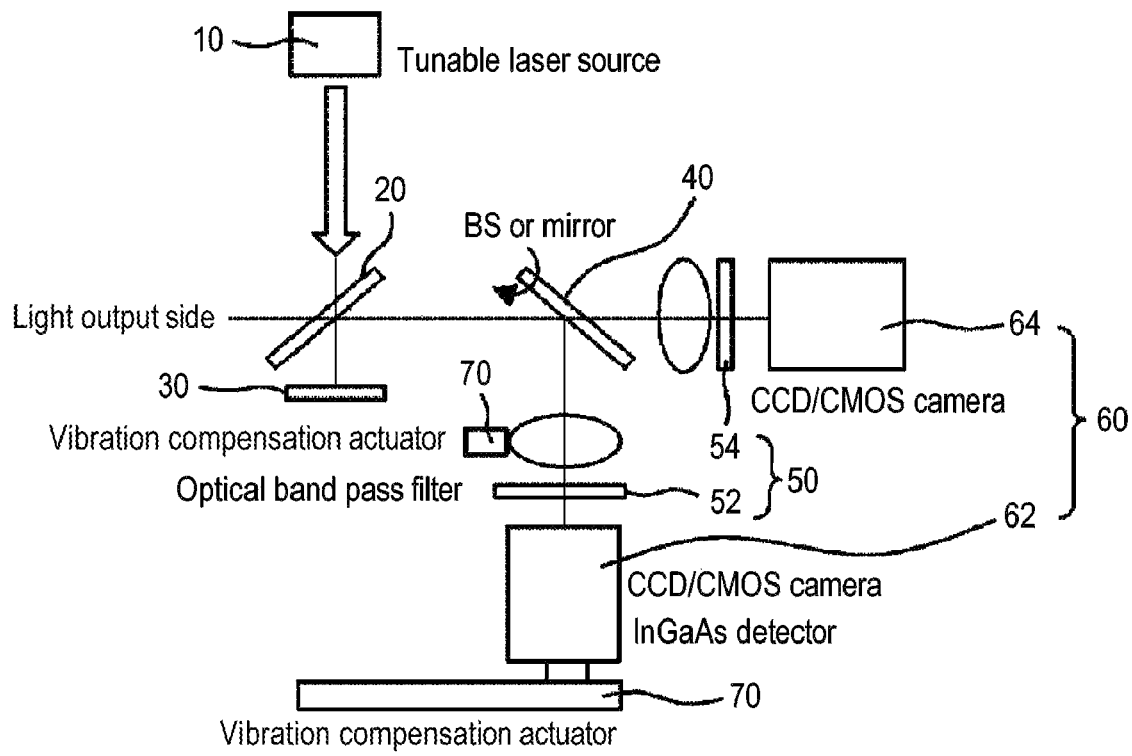
FIG. 3 is a structural diagram of a removable OCT device according to a first embodiment of the present disclosure.

FIG. 3 is a structural diagram of a removable OCT device according to a first embodiment of the present disclosure. The removable OCT device according to the present embodiment is a device mounted at the light output side of an optical device such as an endoscope, a microscope or the like (at the same side as an ocular lens) and simultaneously acquires a visible light image and an OCT image. The removable OCT device includes a tunable laser 10, a first beam splitter 20, a reference mirror 30, a second beam splitter 40, a band pass filter unit 50 and an image detector unit 60. The removable OCT device may further include a vibration compensator 70 and an image processor (not shown).

The tunable laser 10 is a component which emits light to the light output side while tuning the wavelength so that the human body tissue can be taken tomographically by depth, and which makes sure that an infrared ray is reflected from a measurement target object (a human body or the like) to be measured by an optical device (that the light incident on the light output side reaches the measurement target object through the optical device). In some embodiments, the wavelength is tuned in the infrared region of 750 to 1300 nm. As the wavelength grows longer, the depth of infiltration of the light into the human body tissue becomes deeper. Thus, by emitting light while changing the wavelength of the light from a short wavelength to a long wavelength, it is possible to acquire stereoscopic interference signals from the surface of the human body tissue to a predetermined depth. An OCT can be implemented by image-processing the interference signals. The tunable laser 10 may further include an LED, a lamp or the like, which covers a visible ray region, so that the tunable laser 10 can provide a visible ray when the amount of the visible ray emitted from the measurement target object is deficient.

The first beam splitter 20 is a component which generates a reference light (light for setting a phase reference plane) by allowing a portion of the light emitted from the tunable laser 10 to pass through the first beam splitter 20 and to move toward the reference mirror 30, and generates a signal light (a light reflected or emitted from the measurement target object and containing information of the measurement target object) by reflecting a portion of the light emitted from the tunable laser 10 and allowing the light to move toward the light output side. The first beam splitter 20 is configured to reflect the reference light reflected from the reference mirror 30 and is configured to allow the signal light emitted from the light output side to pass through the first beam splitter 20 and to move toward the second beam splitter 40. Information on the measurement target object can be obtained by causing the reference light and the signal light, which are generated by the first beam splitter 20 in this way, to interfere with each other.

The reference mirror 30 is a component which reflects the light passed through the first beam splitter 20 and generates a reference light, namely a light to be compared with phase-shifted signal light.

The second beam splitter 40 is a component which allows a portion of the light emitted from the light output side and the light emitted from the reference mirror 30 to pass through the second beam splitter 40 while it reflects the other portion to divide the optical path into two. Since the second beam splitter 40 is installed on an optical path of the light emitted from the light output side and passed through the first beam splitter 20, the reference light and the signal light are incident on the second beam splitter 40. The removable OCT device according to the present embodiment is configured to simultaneously pass a visible ray of a typical optical device and an infrared ray emitted by the tunable laser 10. Thus, the removable OCT device includes an infrared ray image detector 62 and a visible light image detector 64 in order to separately take an image of the visible ray and the infrared ray. The second beam splitter 40 splits the light to be incident on the infrared image detector 62 and the visible light image detector 64.

The band pass filter unit 50 is a component which filters the light to be incident on the infrared image detector 62 and the visible light image detector 64. The band pass filter unit 50 may include an infrared band pass filter 52 installed on a path of one of the light beams split in the second beam splitter 40 and may further include a visible ray band pass filter 54 installed on a path of the other of the light beams split in the second beam splitter 40. In the removable OCT device according to the present disclosure, the infrared image detector 62 has to receive only an electromagnetic wave of an infrared band as a signal. Thus, it is necessary to provide the infrared band pass filter 52 which passes the light of an infrared band. The visible ray band pass filter 54 is an optional component. In general, a CCD or CMOS image detector is sufficient to take visible light images. Thus, the visible ray band pass filter 54 may be provided when one wishes to enhance the purity of a visible light image by removing the light in the infrared band.

The image detector unit 60 may include an infrared image detector 62 and a visible light image detector 64. On the basis of a travel direction of light, the infrared image detector 62 is installed behind the infrared band pass filter 52, and the visible light image detector 64 is installed behind the second beam splitter 40 or the visible ray band pass filter 54. In this regard, the rear side of the second beam splitter 40 refers to a travel path of the light other than the light which is separated by the first beam splitter 20 and is incident on the infrared image detector 62.

The infrared image detector 62 has to take infrared images in a wavelength range of 750 to 1300 nm. Thus, different types of image detectors are used depending on the wavelength range. Specifically, in the wavelength range of 750 to 1100 nm, a typical CCD or CMOS image detector like the visible light image detector 64 may be used. However, since the typical CCD or CMOS image detector cannot detect an infrared ray of a wavelength of 1100 nm or more, an InGaAs image detector is used. The visible light image detector 64 is an image detector used in a typical digital camera. A CCD or CMOS image detector is used as the visible light image detector 64.

By providing a plurality of infrared ray image detectors 62, it is possible to improve the quality of an OCT image. For example, when images are taken by installing two infrared ray image detectors 62 and synchronizing the image-taking timings thereof, it is possible to obtain two-fold images per unit time and to obtain OCT images having a high quality. When one wishes to obtain images of the same quality, it is possible to shorten the image-taking time by one half. Thus, the images are less susceptible to vibration and are somewhat free from the restrictions in the performance of the vibration compensator 70.

The visible light image detector 64 may be an ocular lens. Since the human eyes may be regarded as one kind of the visible light image detector 64, it is possible to implement an OCT device capable of taking infrared images with the infrared image detector 62 while seeing visible light images through an ocular lens. In this case, the human eyes serve as the visible ray band pass filter 54. Thus, by removing the visible ray band pass filter 54, it is possible to simplify the configuration of the OCT device.

The vibration compensator 70 is a component which compensates the vibration of the lens or the image detector unit 60. The vibration compensator 70 may be an actuator (of hardware type) which mechanically compensates the vibration of the lens or the image detector unit 60 by measuring the vibration, or may be a processor (of software type) which compensates the vibration through image correction by matching the measured images. In the removable OCT device according to the present disclosure, the vibration compensation is needed for the following reason. Due to the characteristics of the OCT device, a plurality of images is taken within a short period of time while tuning the wavelength (namely, while changing the image-taking depth). At this time, if vibration or position shift occurs, an error may be generated in a stereoscopic image. The hardware type vibration compensator 70 is configured to physically cancel the actual vibration. The software type vibration compensator 70 is configured to compensate the error, which is generated in the image due to the vibration, through an image processing process.

The image processor (not shown) is a component which is connected to the image detector unit 60 and configured to process the visible light images and the infrared images acquired in the image detector unit 60. Specific forms of the image processor include a field programmable gate array (FPGA), a digital signal processor (DSP), an ARM, and the like.

Figure 4:
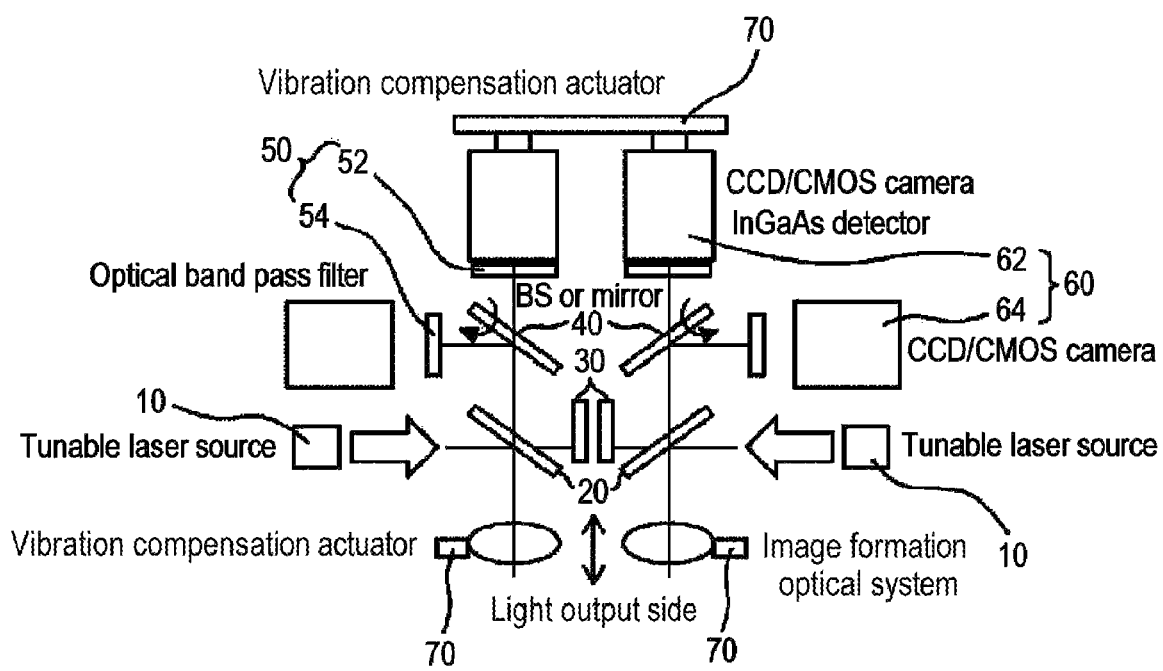
FIG. 4 is a structural diagram of a removable OCT device according to a second embodiment of the present disclosure.

FIG. 4 is a structural diagram of a removable OCT device according to a second embodiment of the present disclosure. The removable OCT device according to the present disclosure is mounted to the light the output side of a binocular optical device. The removable OCT device includes a tunable laser 10, a pair of first beam splitters 20, a reference mirror 30, a pair of second beam splitters 40, a pair of band pass filter units 50 and a pair of image detector units 60. The removable OCT device may further include a vibration compensator 70 and an image processor. It can be said that the removable OCT device according to the second embodiment of the present disclosure is configured to be binocular, namely as a stereo system, by combining, in parallel, two removable OCT devices according to the first embodiment of the present disclosure. Accordingly, the removable OCT device according to the second embodiment of the present disclosure is useful in a device such as a microscope.

In order to take images by separating an infrared ray and a visible ray, the first beam splitters 20, the second beam splitters 40, the band pass filter units 50 and the image detector units 60 are respectively provided in a pair. The tunable laser 10 may be provided in a pair. Since it is desirable to irradiate the same light on an object, it is preferred that there is provided only one tunable laser 10. Furthermore, a pair of reference mirrors 30 may be provided and may be respectively installed at the rear side of the first beam splitters 20. Alternatively, one double-sided mirror may be installed as the reference mirror 30. A pair of vibration compensators 70 and a pair of image processors may be provided, one in each of the image detector units 60. Alternatively, one vibration compensator 70 and one image processor may be provided in the image detector units 60 as a whole.

Figure 5:
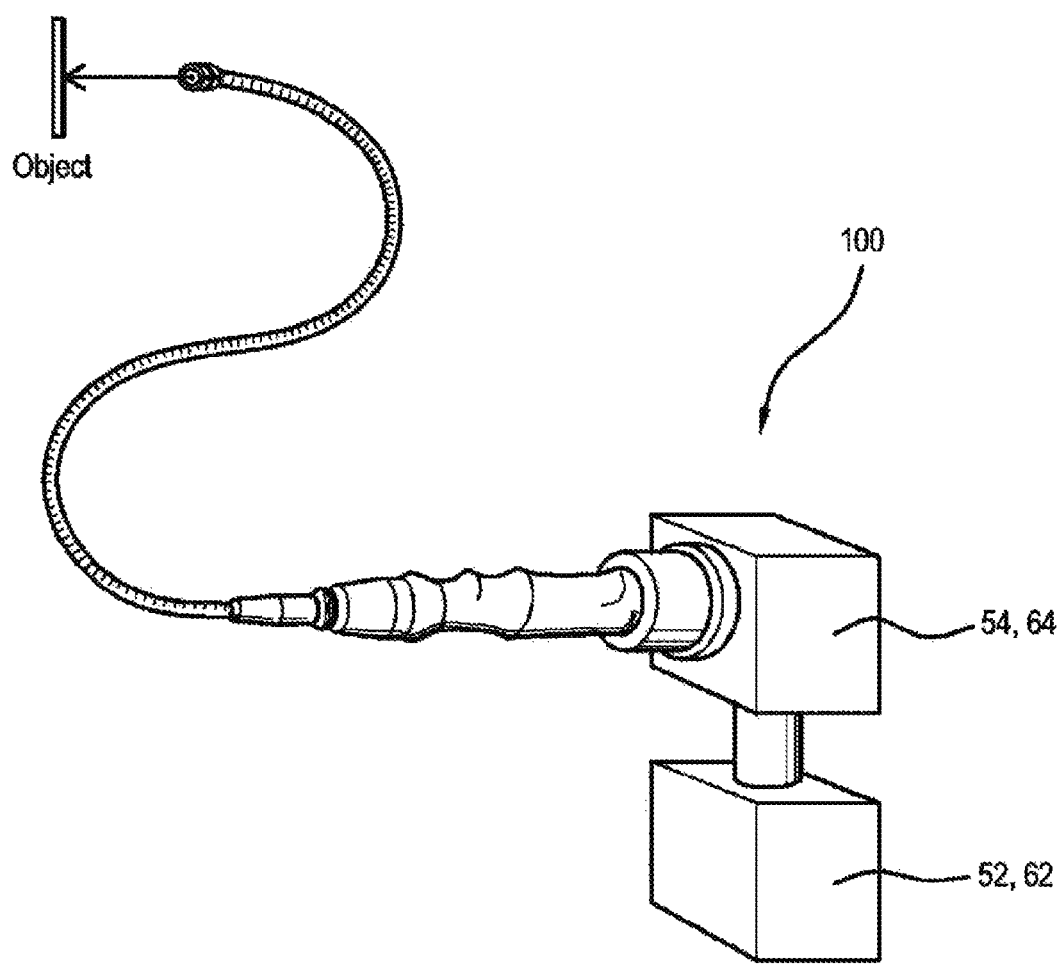
FIG. 5 shows a use state in which the removable OCT device according to the first embodiment of the present disclosure is mounted to an endoscope.
Figure 6:
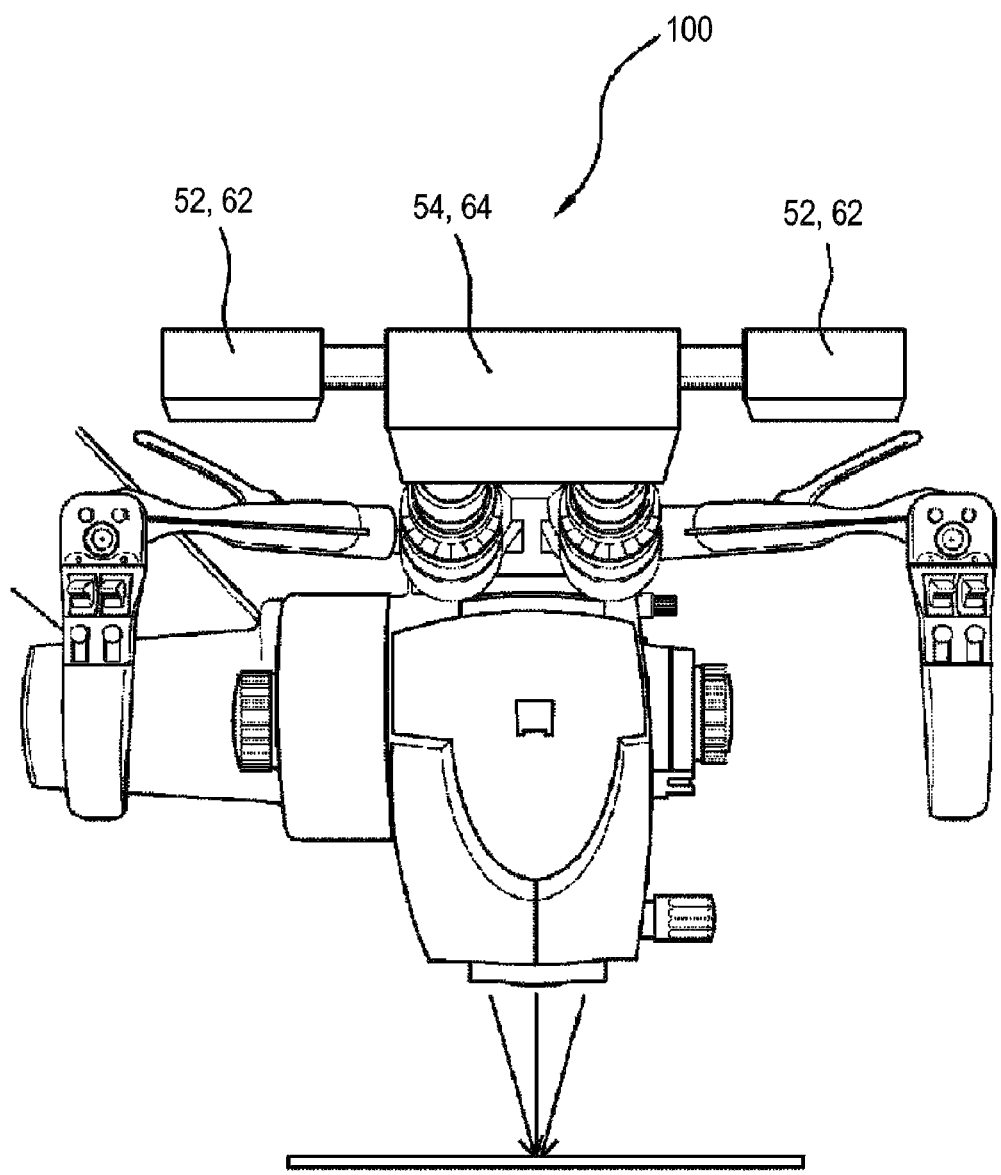
FIG. 6 shows a use state in which the removable OCT device according to the second embodiment of the present disclosure is mounted to a microscope.

FIG. 5 shows a use state in which the removable OCT device according to the first embodiment of the present disclosure is mounted to an endoscope. FIG. 6 shows a use state in which the removable OCT device according to the second embodiment of the present disclosure is mounted to a microscope. It can be noted that the removable OCT device 100 according to the present disclosure can be easily mounted to and removed from an existing optical device such as an endoscope, a microscope or the like.

What is claimed is:

1. A removable OCT device, comprising:
a tunable laser configured to emit light by tuning a wavelength of the light;
a first beam splitter installed on a path of the light emitted from the tunable laser; and
a reference mirror installed on a path of the light that has passed through the first beam splitter,
wherein one side of the removable OCT device is configured to be mounted at a light output side of an optical device where an ocular lens is located so that light reflected by the first beam splitter is irradiated to the ocular lens of the optical device, and the other side of the removable OCT device is not configured to be mounted to the optical device.

2. The device of claim 1, wherein the tunable laser includes a laser having a wavelength which falls within a section of 750 to 1300 nm.

3. The device of claim 1, further comprising:
a second beam splitter installed on a path of the light emitted from the light output side and passed through the first beam splitter.

4. The device of claim 3, further comprising:
a band pass filter unit installed on a path of at least one of light beams split in the second beam splitter.

5. The device of claim 4, wherein the band pass filter unit includes a visible ray band pass filter installed in a first path of the light split by the second beam splitter.

6. The device of claim 5, further comprising:
an image detector unit including a visible light image detector disposed at a rear side of the visible ray band pass filter.

7. The device of claim 6, wherein the visible light image detector is an ocular lens.

8. The device of claim 6, further comprising:
a vibration compensator configured to compensate vibration of the image detector unit.

9. The device of claim 8, wherein the vibration compensator is an actuator configured to mechanically compensate the vibration of the image detector unit by measuring the vibration.

10. The device of claim 8, wherein the vibration compensator is a processor configured to compensate the vibration by matching and correcting measured images.

11. The device of claim 4, wherein the band pass filter unit includes an infrared band pass filter installed in a second path of the light split by the second beam splitter.

12. The device of claim 11, further comprising:
an image detector unit including an infrared ray image detector disposed at a rear side of the infrared band pass filter.

13. The device of claim 12, wherein the image detector unit includes a plurality of infrared ray image detectors.

14. A removable OCT device comprising:
a first tunable laser configured to emit first light by tuning a wavelength of the first light;
a second tunable laser configured to emit second light by tuning a wavelength of the second light;
a first beam splitter installed on a path of the first light emitted from the first tunable laser;
a second beam splitter installed on a path of the second light emitted from the second tunable laser;
a first reference mirror installed on a path of the first light that has passed through the first beam splitter; and
a second reference mirror installed on a path of the second light that has passed through the second beam splitter,
wherein one side of the removable OCT device is configured to be mounted at two light output sides of an optical device for dual eyes and the other side of the removable OCT device is not configured to be mounted to the optical device,
wherein the first tunable laser is configured to emit the first light to one of the two light output sides of the optical device, and
wherein the second tunable laser is configured to emit the second light to the other of the two light output sides of the optical device.

15. A removable OCT device comprising:
a first tunable laser configured to emit first light by tuning a wavelength of the first light;
a second tunable laser configured to emit second light by tuning a wavelength of the second light;
a first beam splitter installed on a path of the first light emitted from the first tunable laser;
a second beam splitter installed on a path of the second light emitted from the second tunable laser; and
a double-sided mirror installed on a path of the first light that has passed through the first beam splitter and a path of the second light that has passed through the second beam splitter,
wherein one side of the removable OCT device is configured to be mounted at two light output sides of an optical device for dual eyes and the other side of the removable OCT device is not configured to be mounted to the optical device,
wherein the first tunable laser is configured to emit the first light to one of the two light output sides of the optical device, and wherein the second tunable laser is configured to emit the second light to the other of the two light output sides of the optical device.

\* \* \* \* \*